United States Patent [19]

Furutani

[11] Patent Number: 5,322,920
[45] Date of Patent: Jun. 21, 1994

[54] THERMOSETTING ESTERIMIDE OLIGOMER AND ITS PRODUCTION METHOD

[75] Inventor: Hiroyuki Furutani, Ohtsu, Japan

[73] Assignee: Kanegafuchi Kagaku Kogyo Kabushiki Kaisha, Osaka, Japan

[21] Appl. No.: 735,218

[22] Filed: Jul. 24, 1991

[30] Foreign Application Priority Data

Jul. 25, 1990 [JP] Japan ................................ 2-196888
Jul. 25, 1990 [JP] Japan ................................ 2-196889

[51] Int. Cl.$^5$ .................... C08G 63/66; C08G 69/44
[52] U.S. Cl. .................................. 528/288; 528/289; 528/296; 528/298; 528/299; 528/300; 528/307; 528/308; 528/308.6
[58] Field of Search ............... 528/288, 289, 296, 298, 528/299, 300, 307, 308, 308.6; 525/432

[56] References Cited

U.S. PATENT DOCUMENTS

| | | | |
|---|---|---|---|
| 3,852,246 | 12/1974 | Schmidt et al. | 528/289 |
| 4,290,929 | 9/1981 | McGregor et al. | 528/288 |
| 4,362,861 | 12/1982 | Shen | 528/289 |
| 4,757,118 | 7/1988 | Das et al. | 528/153 |
| 4,861,857 | 8/1989 | Kricheldorf et al. | 528/184 |

FOREIGN PATENT DOCUMENTS 53-119865 10/1978 Japan.
1-123819 5/1989 Japan.

OTHER PUBLICATIONS

Fujisawa, *Plastics*, vol. 34, No. 7, pp. 75-81 (Jul. 1983).
Kurita et al., *Polymer Applications*, 37/2 (Feb. 1988), pp. 74-79.
Takeich, *Polymer Forming*, 37/7 (Jul. 1988), pp. 347-354.
Flory, Paul J., *Principles of Polymer Chemistry*, pp. 74-91 (Sep. 3, 1953).
Cannizzo et al., 15 *Makromol. Chem., Suppl.* 85-91 (Jun. 1989).
Tanaka et al., "Synthesis of Polyamic Acids from Trimellitic Anhydride and Bisphenols with Diamines by a One-Pot Method", *Proceedings of Third Int'l Conf. on Polyimides*, pp. 65-68 (Nov. 2-4, 1988).

Primary Examiner—John Kight, III
Assistant Examiner—Jeffrey Culpeper Mullis
Attorney, Agent, or Firm—Armstrong, Westerman, Hattori, McLeland & Naughton

[57] ABSTRACT

Thermosetting esterimide oligomers of formulas (IA) and (IB) are disclosed:

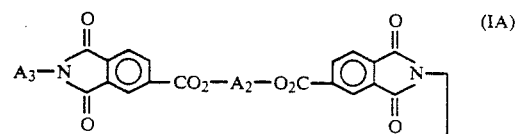

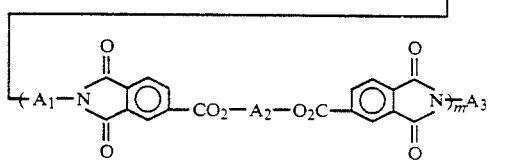

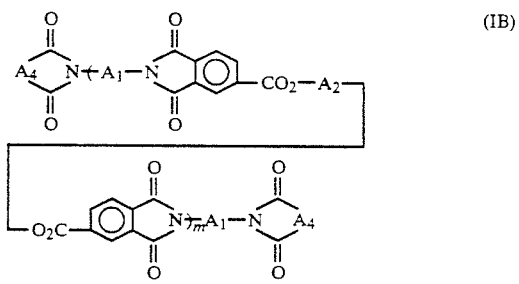

where $A_1$, $A_2$ and $A_4$ are divalent organic groups, $A_3$ is a monovalent organic group and $A_1$, $A_2$, $A_3$ and $A_4$ may be the same or different, with m being an integer of 1-30. The above compounds provide hard substances having excellent workability, heat resistance and mechanical properties.

6 Claims, No Drawings

THERMOSETTING ESTERIMIDE OLIGOMER AND ITS PRODUCTION METHOD

BACKGROUND OF THE INVENTION

The present invention relates to a new thermosetting compound and its production method. More particularly, it relates to an esterimide oligomer having excellent heat resistance and also having an appropriate reactivity for lamination and molding, and a production method thereof.

Thermosetting resins have been used for various kinds of electric insulation materials and structural materials for cast molding, impregnation, lamination and molding. Recently, conditions in these usages have become increasingly more severe. Especially, the heat resistance of the materials has become an important property. Formerly, for such usage, a thermosetting polyimide resin or a heat-resistant epoxy resin has been used. Among them, as the thermosetting polyimide resin, "Kerimid" (trade name, manufactured by Rhône-Poulenc Chemie) mainly composed of a bismaleimide compound and diaminodiphenylmethane is used (Matsuo Fujisawa, Plastics, Vol. 34, No. 7, page 75, 1983). However, the thermosetting polyimide resin has a disadvantage of needing a high temperature and a long heating time during forming. In addition, as diaminodiphenylmethane is harmful to a human body, there is a problem of sanitation in handling. In addition, recently, an acetylene terminated type polyimide has been put on the market as "Thermid" (trade name, manufactured by Gulf R&D, Japanese Laid-Open Publication No. 53-119865). However, because its organic solvent solubility is comparatively low, high boiling point polar organic solvents such as dimethylformamide and dimethylacetamide must be used, and thus, there is a problem in handling.

In order to solve the problem encountered with the polyimide, numerous improvement methods have been proposed for the resin, and among them, various kinds of polyesterimide resin have been proposed from viewpoints of
(for example, U.S. Pat. Nos. 4,757,118, 4,362,861, 3,852,246 or Japanese Laid-Open Publication No. 1-123819).

However, it is pointed out that generally, the polyesterimide is lower in softening point and more excellent in resin flowing property than the polyimide, but inferior in heat resistance to the polyimide [Keisuke Kurita et al., Polymer Applications, Vol. 37, No. 2, pgs. 22-26, (1989)].

A new acid dianhydride with ester bonding was at first synthesized using trimellitic acid anhydride as a starting monomer and paratoluenesulfonic acid chloride/pyridine as a reaction solvent, then polyesterimide is synthesized in the same reaction system by introducing diamine therein [H. Tanaka et al., Proceedings/Abstracts of Third International Conference on Polyimides, pgs. 65-68, (1988)]. However, there is no knowledge at all about thermosetting polyesterimides or their reactivity such as photo-reactivity.

SUMMARY OF THE INVENTION

An object of the present invention is to provide an esterimide oligomer, which gives hard substances having excellent molding properties, and having high heat resistance and mechanical properties.

Other objects and advantages of the present invention will be made clear through reading the following detailed description.

The present inventors have made an extensive series of studies and found out that the above objects can be attained by, at first, synthesizing a new acid dianhydride with ester bonding using trimellitic acid anhydride as a starting monomer and paratoluenesulfonic acid chloride/pyridine as a reaction solvent, then reacting the acid dianhidride with a diamine, further adding a primary amine or an acid anhydride to terminate its ends, and then ring-closing and dehydrating the reaction product.

DETAILED DESCRIPTION OF THE INVENTION

The present invention is, in a first aspect, to provide a thermosetting compound of formula (IA):

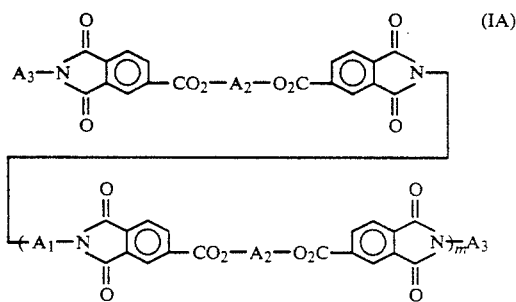

wherein $A_1$ and $A_2$ are divalent organic groups, $A_3$ is a monovalent organic group and $A_1$, $A_2$ and $A_3$ may be the same or different, with m being an integer of 1-30).

The present invention is, in a second aspect, to provide a thermosetting compound of formula (IB):

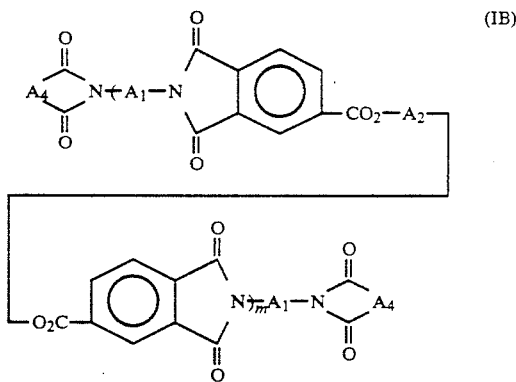

wherein $A_1$, $A_2$ and $A_4$ are divalent organic groups, and $A_1$, $A_2$ and $A_4$ may be the same or different, with m being an integer of 1-30.

The present invention is, in a third aspect, to provide a production method of a thermosetting compound, characterized in the following: a reaction system is kept at room temperature or below in an inert gas atmosphere, trimellitic acid anhydride dissolved in an aprotic polar solvent is added to a solution mixed with paratoluenesulfonic acid chloride and pyridine, than diol dissolved in advance in the aprotic polar solvent is reacted, then the necessary amount of a diamine dissolved in the aprotic polar solvent, which is required for obtaining both end acid anhydrides-terminated telechelic oligoesteramic acid, is added to allow the reaction proceed, further, a primary amine or an acid anhydride dissolved in the aprotic polar solvent is added to terminate both ends, then, a non-solvent is added to dehydrate and close the rings of the reaction product.

To begin with, a production method of a thermosetting compound of the present invention is described.

The necessary quantity of paratoluenesulfonic acid chloride (hereinafter described as TsCl) is weighed in an inert gas atmosphere such as argon, nitrogen, etc., a reaction system is kept at room temperature or below, preferably below 10° C., more preferably below freezing temperature, and then pyridine is dropped through a cylinder while paying attention to heat generation. After enough reaction, the calculated quantity of trimellitic acid anhydride (hereinafter described at TMA) is dissolved in an aprotic polar solvent and added. Then, a diol of formula (II), $$HO-A_2-OH \quad (II)$$

wherein $A_2$ is a divalent organic group is dissolved in the same aprotic polar solvent at freezing temperature and then added. To complete the reaction, the reaction is properly accelerated at room temperature. In this step, to obtain a copolymer, it is possible to add an organic tetracarboxylic acid dihydride of formula (III):

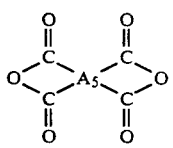

(III)

wherein $A_5$ is a tetravalent organic group.

Then, the system is again cooled at freezing temperature, and a diamine of formula (IV), which was dissolved in the same aprotic polar solvent, is added:

$$H_2N-A_1-NH_2 \quad (IV)$$

wherein $A_1$ is a divalent group. It is important to add the calculated quantity of diamine to obtain both end acid anhydride groups-terminated telechelic oligoesteramic acid solution. After the oligoesteramic acid solution is thoroughly reacted, the reaction is further continued in a reaction system.

Thereafter, an oligoesteramic acid of formulas (VIA) or (VIB) is synthesized, wherein the end acid anhydrides are terminated by a primary amine of formula (VA) or by an aromatic acid anhydride of formula (VB), dissolved in the same aprotic polar solvent.

$$A_3-NH_2 \quad (VA)$$

wherein $A_3$ is a monovalent organic group.

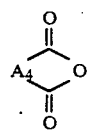

(VB)

wherein $A_4$ is a divalent organic group.

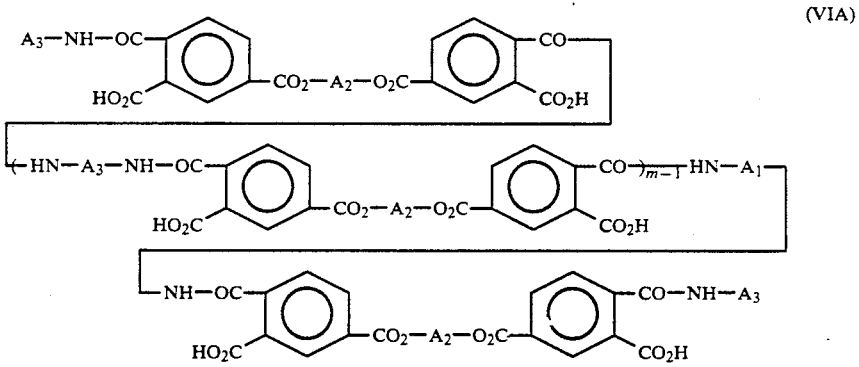

(VIA)

wherein $A_1$ and $A_2$ are divalent organic groups, $A_3$ is a monovalent organic group and $A_1$, $A_2$ and $A_3$ may be the same or different, with m being an integer of 1-30.

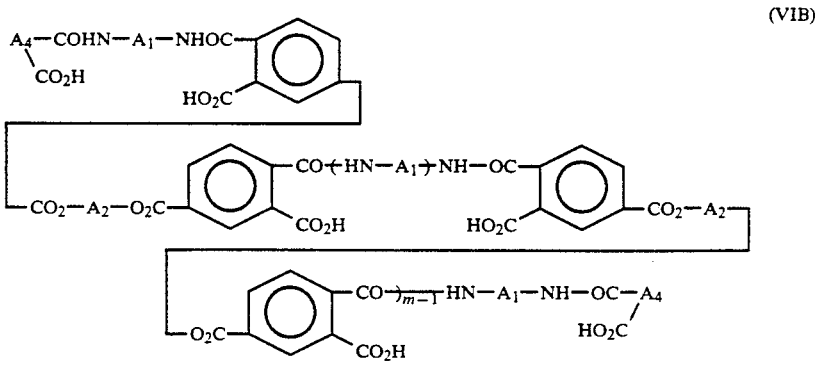

(VIB)

wherein $A_1$, $A_2$ and $A_3$ are divalent organic groups, and $A_1$, $A_2$ and $A_4$ may be same or different, with m being an integer of 1-30.

Finally, in order to subject said amic acid solution to dehydration and ring closure thermally or chemically, a non-solvent is added to transform it into an esterimide oligomer of formula (IA) or (IB) under reflux and azeotropic conditions.

The non-solvents used in this step may include aromatic hydrocarbons such as xylene, toluene and benzene, but benzene is preferably used. Upon the reaction, azeotropically distilled water is circulated by Dean-Stark reflux condenser until the theoretical reaction quantity of water is collected. After the reaction, the resulting polyimide solution is poured into violently stirred water or an alcohol-based solvent, and polyimide is precipitated as powder. The powder is collected by filtration and dried for 48 hours at 80° C. under reduced pressure.

As organic tetracarboxylic acid dianhydrides used in the present invention, those having any structure can be used, but $A_5$ in the above formula (III) is preferably a tetravalent organic group and aromatic group. This $A_5$ group may be exemplified as follows:

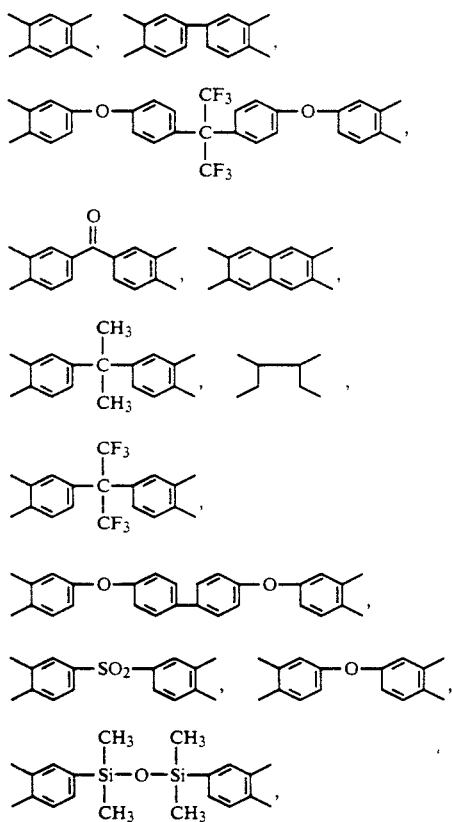

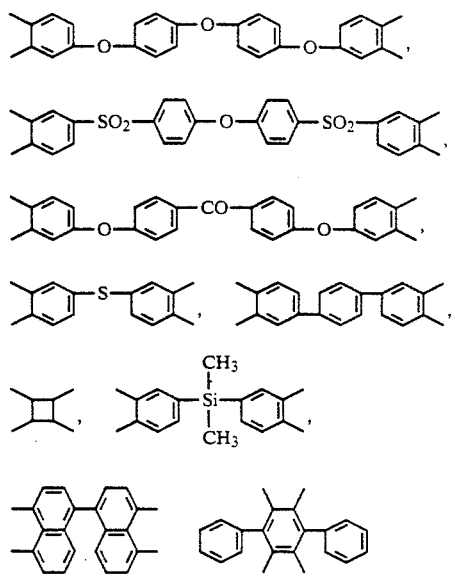

These organic tetracarboxylic acid dianhydrides may be used singly or in combination of two or more. More particularly, it is preferably, from the viewpoint of balance of various properties, to use as main components at lest one of the following:

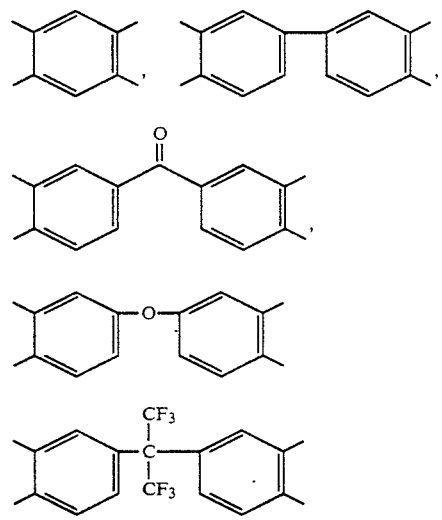

The diols used in the present invention are expressed by formula (II), $$HO-A_2-OH \qquad (II)$$

wherein $A_2$ is a divalent organic group. $A_2$ may be any divalent organic group, examples of which are as follows:

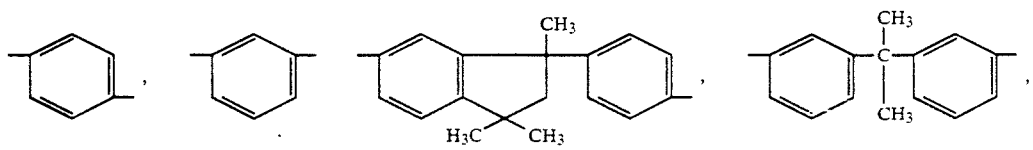

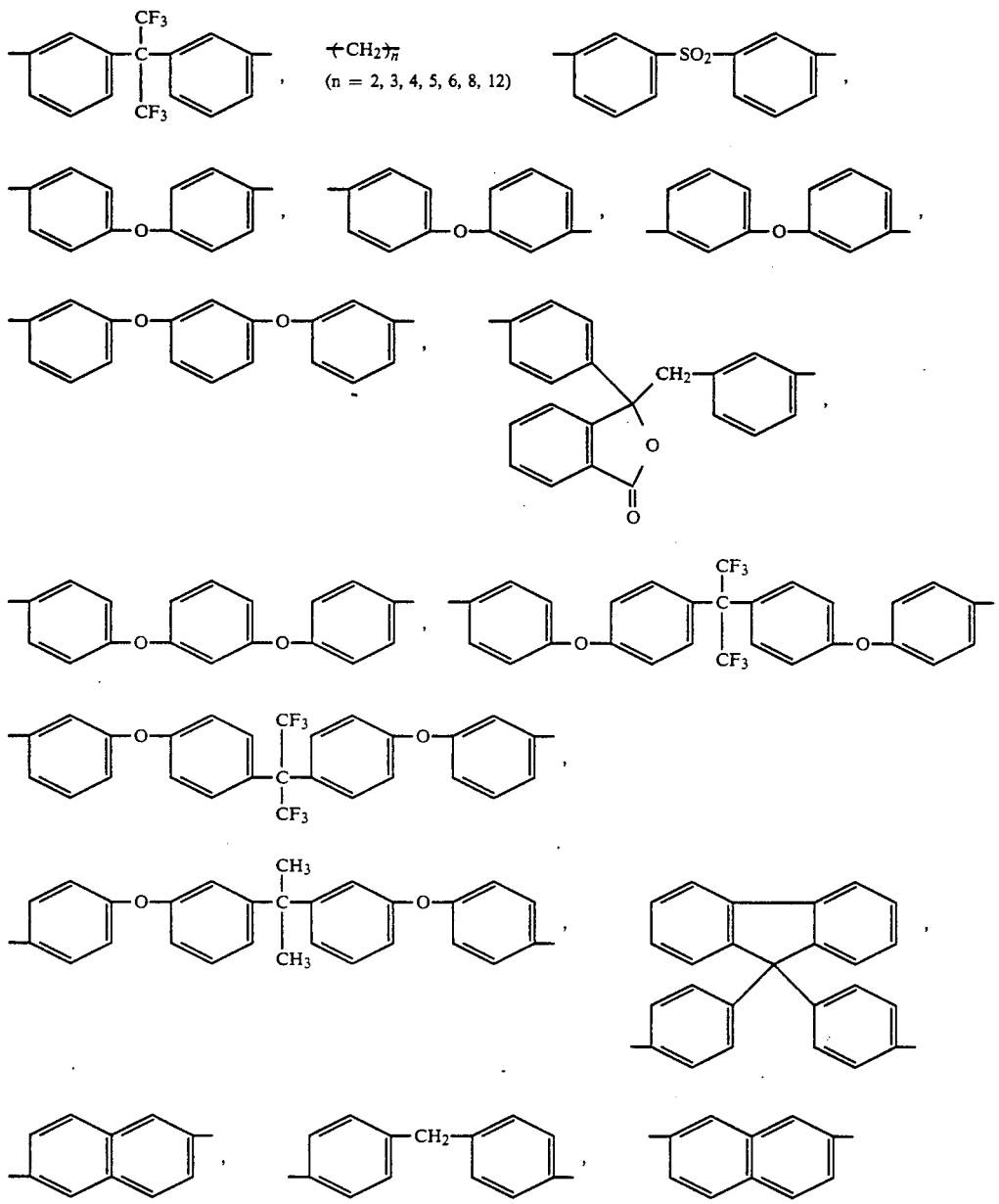
Among them, the aromatic group is preferred, and it is preferable to use as a main component at least one of the following:
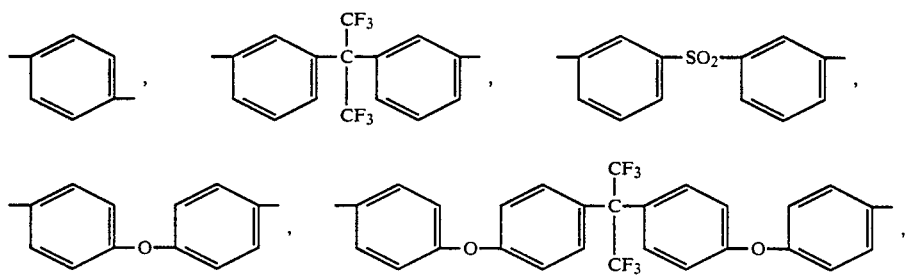
The diamines used in the present invention are expressed by formula (IV),
$$H_2N-A_1-NH_2 \qquad (IV)$$
wherein $A_1$ is a divalent organic group. $A_1$ may be any divalent organic group, examples of which are as follows:

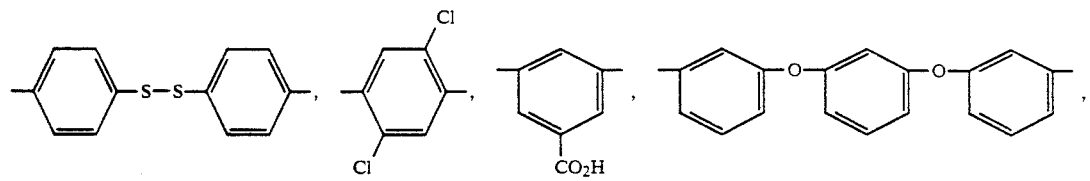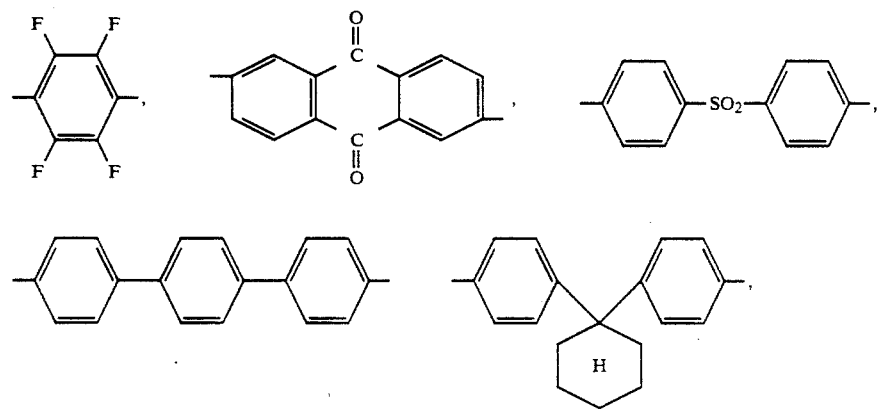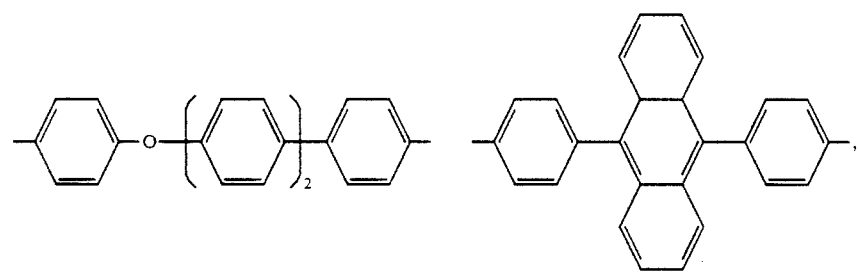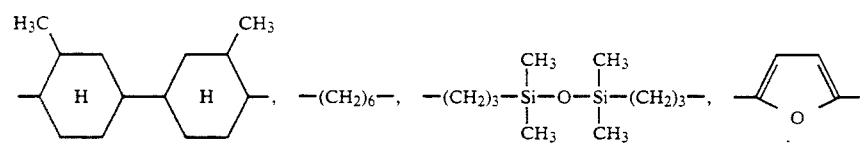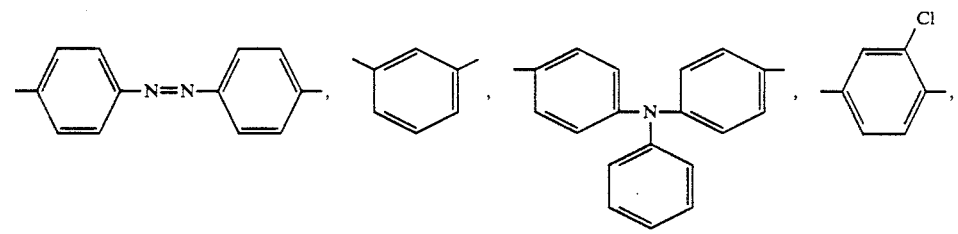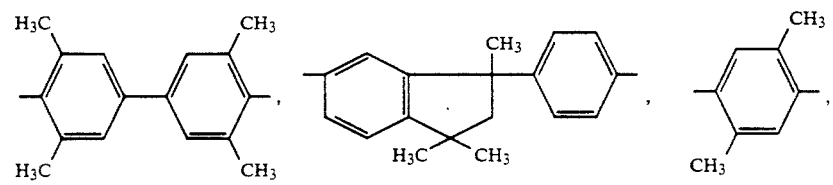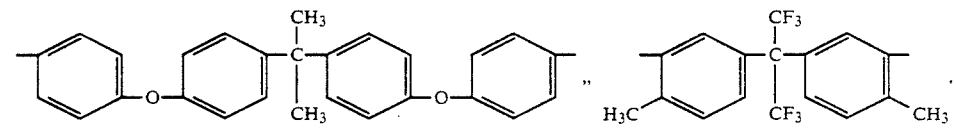

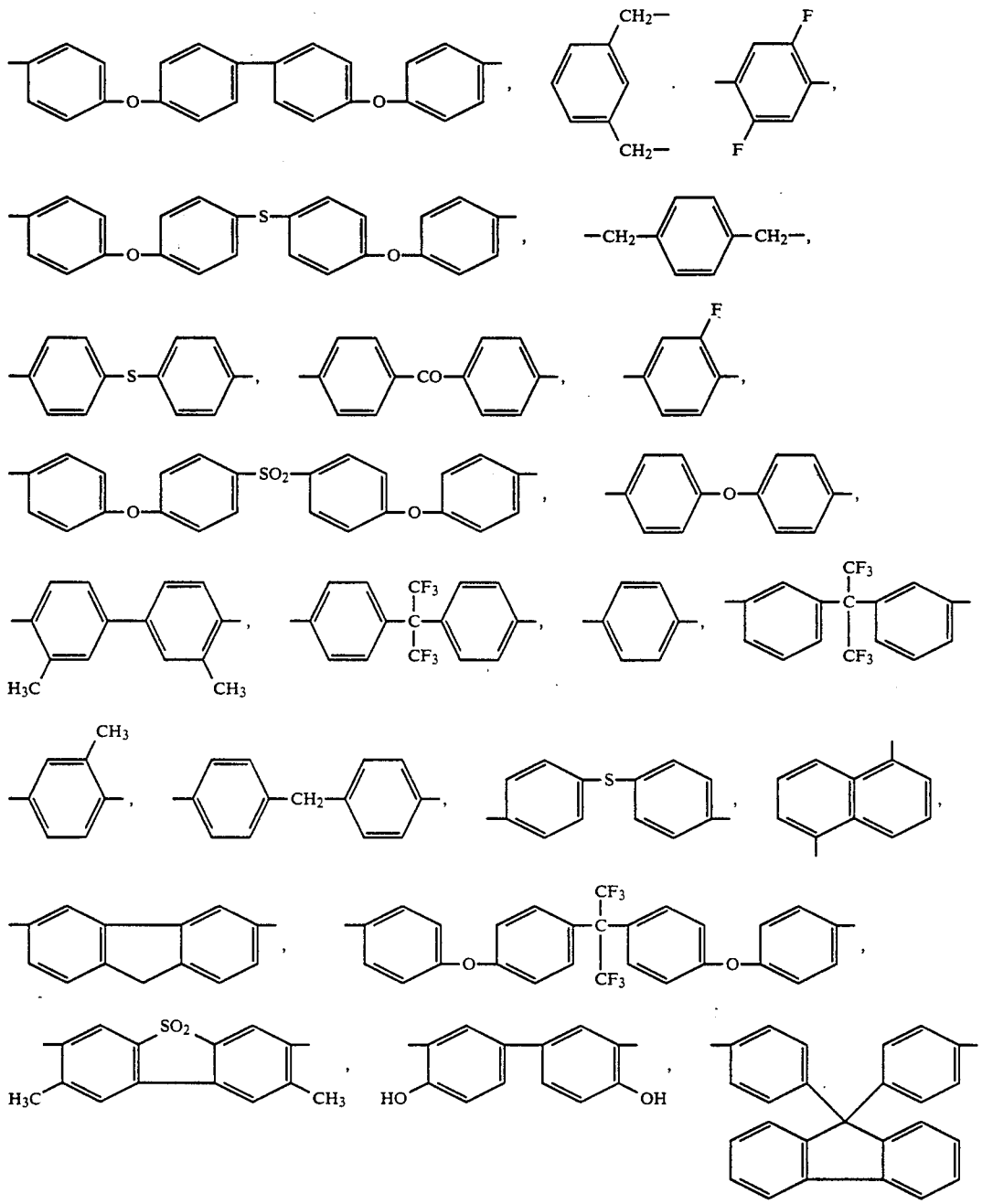
Among them, the aromatic group is preferred, and it is preferable to use as a main component at least one of the following:
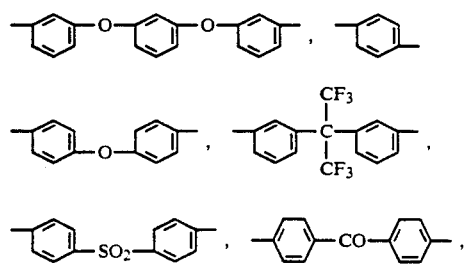
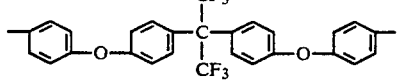
The primary amines for the end termination used in the present invention are expressed by formula (VA),
$$A_3-NH_2 \qquad (VA)$$
and $A_3$ of the primary amines are exemplified as follows:

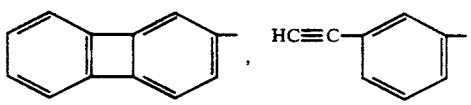 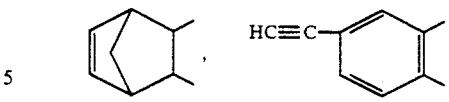

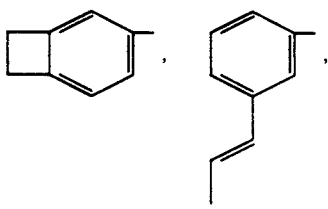

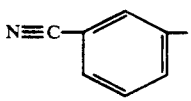

But, the following are especially preferred in respect of cost and handling:

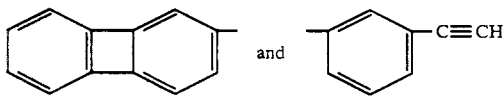

The aromatic acid anhydrides for the end termination used in the present invention are expressed by formula (VB), $$\underset{O}{\overset{O}{\underset{\|}{A_4}}}\underset{\|}{\overset{\|}{\underset{O}{\bigg\rangle}}}O \qquad (VB)$$

and $A_4$ of the aromatic acid anhydrides are exemplified as follows:

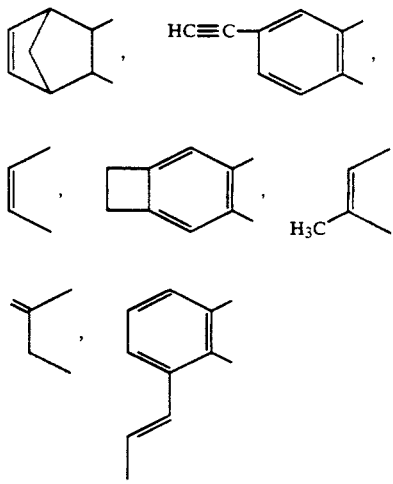

But, the following are especially preferred in respect of cost and handling:

As the aprotic polar organic solvents used in the reaction for obtaining an oligoesteramic acid solution, there are, for example, sulfoxide solvents such as dimethylsulfoxide and diethylsulfoxide; formamide solvents such as N,N'-dimethylformamide and N,N'-diethylformamide; and acetamide solvents such as N,N'-dimethylacetamide and N,N'-diethylacetamide. These can be used singly or in combination of two or more. Besides, not only these aprotic polar solvents but also their mixed solvent with polyamic acid non-solvents such as methanol, ethanol, isopropanol and benzene methyl cellosolve can be used. It is preferable to use dimethylformamide (hereinafter, described as DMF) in respect of tint and yield of polymer generated. The mechanism is not made clear why a reactive esterimide oligomer, relating to the present invention, gives a hard substance with especially high heat resistance. But, it is said that the mechanism is due to benzene skeleton formation by thermosetting (trimerization) of acetylene or tetrabenzocyclooctadiene skeleton formation by thermosetting (dimerization) of biphenylene [for example, Tsutomu Takeich, *Polymer Forming*, Vol. 37, No. 7, p. 347 (1988)].

In order to control the number average polymerization degree [DP; P. J. Flory, *Principles of Polymer Chemistry*: Cornell University Press: Ithaca, N.Y., p. 91 [1953)], the polymerization ratio n is 1-30, preferable 1-25, or more preferably 1-20. If the value is over the upper limit, a problem of lowered organic solvent solubility occurs. If the value is less than the lower limit, there occurs a problem in mechanical strength. Upon obtaining hard substances from an esterimide oligomer of the present invention, epoxy resins, epoxy resin curing agents, hardening accelerators, fillers, flame retarders, reinforcing agents, surface treating agents, pigment and various elastomers can be conjointly used.

The epoxy resins are compounds having two or more epoxy (glycidyl) groups in their molecules. Examples are novolak type epoxy resins which are reaction products of formaldehyde, phenols such as phenol and orthocresol, and glycidylether compounds derived from halogenated polyphenols such as novolak derived from tetrabromobisphenol A, bromopolyphenols and divalent or more valent phenols such as bisphenol A, bisphenol F, hydroquinone, resorcin, fluruglycine, tris-(4-hydroxyphenyl) methane and 1,1,2,2,-tetrakis (4-hydroxyphenyl) ethane; amine type epoxy resins derived from aniline, paraaminophenol, metaaminophenol, 4-aminometacresol, 6, amine-metacresol, 4-4'-diaminodiphenylmethane, 8,8'-diaminodiphenylmethane, 4,4'-diaminodiphenylether, 3,4'-diaminodiphenylether, 1,4-bis (4-aminophenoxy) benzene, 1,4-bis(3-aminophenoxy)benzene, 1,3-bis (3-aminophenoxy)benzene, 2,2-bis(4-aminophenoxyphenyl)propane, para-phenylenediamine, metaphenylenediamine, 2,4-toluenediamine, 2,6-toluenediamine, paraxylenediamine, metaxylenediamine, 1,4-cyclohexane-bis(methylamine), 1,4-cyclohexane-bis(methylamine), 5-amino-1-(4'-aminophenyl)-1, 8,8-trimethylindan, 6-amino-1-(4-aminophenyl)-1 and 8,8-trimethylindane; hydantoin type epoxy resins derived from aromatic carboxylic acids such as 5,5-dimethylhydantoin and glycidylester compounds derived from aromatic carboxylic acids such as paraoxybenzoic acid, terephthalic acid and isophthalic acid; alicyclic epoxy resins such as 2,2'-bis(3,4-epoxycyclohexyl)propane, 2,2-bis[4-(2,3-epoxypropyl)cyclohexyl]propane, vinylcyclohexenedioxide and 3,4-epoxycyclohexanecarboxylate; and triglycidylisocyanurate and 2,4,6-triglycidoxy-s-triazine. These compounds may be used singly or in combination of two or more.

Examples of the epoxy hardening agents include amine type hardening agents such as aromatic amines ening agents may be used singly or in combination of two or more.

Examples of the hardening accelerators include amines such as benzyldimethylamine, 2,4,6-tris(dimethylaminomethyl) phenol, 1,8-diazabicycloundecene; imidazole compounds such as 2-ethyl-4-methylimidazole; and borontrifluoride-amine complex. These hardening accelerators may be used singly or in combination of two or more.

It is effective to add elastomers to improve mechanical strength. The elastomers may be exemplified as follows:

Silostic

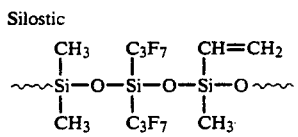

Sylgord

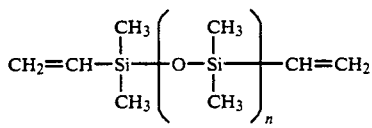

ATBN

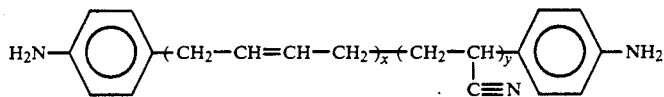

ATS

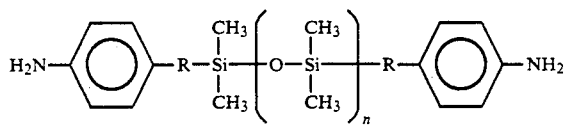

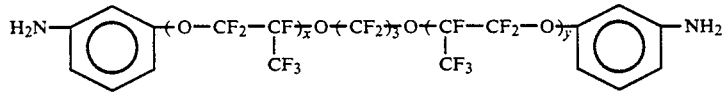

3F  (X + Y = 3)

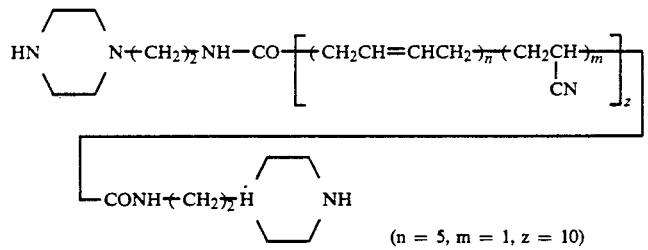

(n = 5, m = 1, z = 10)

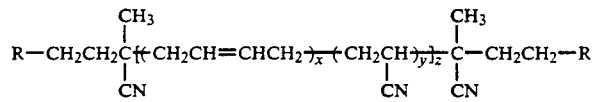

R: —COOH (CTBN, CTB)

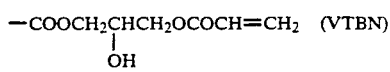

such as xylylenediamine and aliphatic amines; polyphenol compounds such as phenolnovolak and cresolnovalak; and hydrazide compounds. These epoxy hardening agents Among elastomers described above, Silostic (LS-420) and Sylgord (184) are manufactured by Dow Corning Co., Ltd., Hiker. ATBN (1300×16 etc.), CTB (2000×162), CTBN (1300×13, 1300×8, 1300×31) and VTBN (1330×23) are manufactured by Ube Kosan Co., Ltd., and 3F is manufactured by Monsanto Co., Ltd.

Examples of the fillers include aluminum hydroxide, antimony trioxide and red phosphorus. Examples of the reinforcing materials include woven cloth, non-woven cloth and mat made of carbon fiber, glass fiber, aramide fiber and liquid crystal polyester fiber such as vectra, polybenzothiazole (PBT) fiber and alumina fiber, and paper.

In the following, the present invention will be explained in more detail by way of examples, but the present invention is not limited thereto.

Abbreviations to be used in the examples are as follows.

The organic group $A_2$ of aromatic diol compounds (I) expressed by formula (II), $$HO-A_2-OH \quad (II)$$
[1]

are as follows:

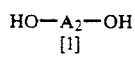  1aA

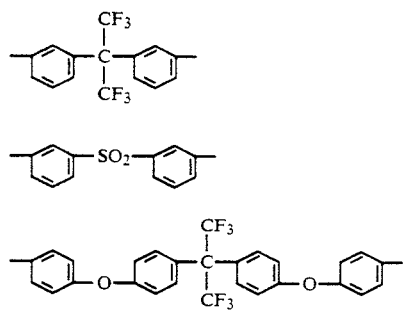  1bA

1cA

The organic group $A_1$ of aromatic diamine compounds of formula (IV)

$$H_2N-A_1-NH_2 \quad (IV)$$
[3]

are as follows:

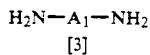  3aA

3bA

3cA

And, the organic group $A_3$ of primary amines (4) of formula (VA)

$$A_3-NH_2 \quad (VA)$$
[4]

are as follows:

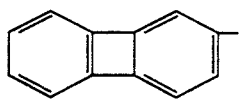  4aA

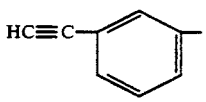  4bA

And, the organic group $A_4$ of acid anhydrides (4) of formula (VB)

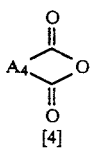  (VB)

[4]

are as follows;

  4aB

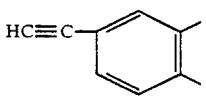  4bB

EXAMPLE 1

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to the reaction system, replacement with argon was sufficiently made. The reaction system was cooled to freezing temperature, and 30 ml of dried pyridine were added while paying attention to heat generation. 15 g (78 mmol) of TMA were completely dissolved in 110 ml dried DMF, and then the solution was added in 30 min. At that temperature, the reaction was continued, and 13.1 g (39 mmol) of the aromatic diol 1aA. which was dissolved in 30 ml dried DMF, were added dropwise at freezing temperature. After 30 min., an ice bah was removed, and the reaction was continued for 1 hour at room temperature. Then, the reaction system was again cooled to freezing temperature, and 5.69 g (19.5 mmol) of the aromatic diamine 3aA were added to 50 ml dried DMF. After 30 min., the ice bath was removed, and the reaction system was heated to 60° C. using an oil bath and the reaction was continued for 30 min. 7.06 g (39.0 mmol) of the aromatic primary amine 4aA were added to 10 ml dried DMF and reacted for 2.6 hours. Then, 200 ml dried benzene was added and 1.2 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5aA was filtered under reduced pressure and dried for 48 hours at 80° C. in vacuum, 29.6 g (yield; 74.9%) of pale yellow powder were obtained.

Using 4.5 g of this esterimide oligomer 5aA, press molding was carried out under 170° C.×10 kg/cm² ×1.5 hours. Then, a cast molding plate with 12 mm (width)×12 cm (length)×1.5 mm (thickness was obtained. The results of measurement of various properties of the esterimide oligomer 5aA and the cast molded plate are set forth in Table 1 and Table 2.

EXAMPLE 2

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to the reaction system, replacement with argon was sufficiently made. The reaction system was cooled to freezing temperature, and 30 ml of dried pyridine were added while paying attention to heat generation. 15 g (78 mmol) of TMA were completely dissolved in 110 ml dried DMF, and then the solution was added in 30 min. At that temperature, the reaction was continued, and 9.75 g (39 mmol) of the aromatic diol 1bA, which was dissolved in 30 ml dried DMF, were added dropwise at freezing temperature. After 30 min., an ice bath was removed, the reaction was continued for 1 hour at room temperature. Thereafter, the reaction system was again cooled to freezing temperature, and 6.51 g (19.5 mmol) of the aromatic diamine 3bA were added to 50 ml dried DMF. After 30 min., the ice bath was removed, the reaction system was heated to 60° C. using an oil bath and the reaction was continued for 30 min. 5.11 g (39.0 mmol) of the aromatic primary amine 4bA were added to 10 ml dried DMF and reacted for 2.6 hours. Then, 200 ml dried benzene was added and 1.3 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5bA was filtered under reduced pressure and dried for 48 hours at 80° C. in vacuum, 33.9 g (yield; 96.7%) of pale yellow powder were obtained.

Using 4.5 g of this esterimide oligomer 5bA. press molding was carried out under 180° C.×10 kg/cm²×1.5 hours. Then, a cast molded plate with 12 mm (width)×12 cm (length)×12.mm (thickness) was obtained. The results of measurement of various properties of the esterimide oligomer 5bA and the cast molded plate are set forth in Table 1 and Table 2.

EXAMPLE 3

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to the reaction system, replacement with argon was sufficiently made. The reaction system was cooled to freezing temperature, and 30 ml of dried pyridine were added while paying attention to heat generation. 15 g (78 mmol) of TMA were completely dissolved in 110 ml dried DMF, and then the solution was added in 30 min. At that temperature, the reaction was continued, and 20.0 g (39 mmol) of the aromatic diol 1cA. which was dissolved in 30 ml dried DMF, were added dropwise at freezing temperature. After 30 min., an ice bath was removed, the reaction was continued for 1 hour at room temperature. Thereafter, the reaction system was again cooled to freezing temperature, and 4.84 g (19.5 mmol) of the aromatic diamine 3cA were added to 50 ml dried DMF. After 30 min., the ice bath was removed, the reaction system was heated to 60° C. using an oil bath and reaction was continued for 30 min. 7.06 g (39.0 mmol) of the aromatic amine 4aA were added to 10 ml dried DMF and reacted for 2.6 hours. Then, 200 ml dried benzene were added and 1.4 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5cA was filtered under reduced pressure and dried for 48 hours at 80° C. in vacuum, 43.2 g (yield; 94.3%) of pale yellow powder were obtained.

Using 4.5 g of this esterimide oligomer 5cA, press molding was carried out under 180° C.×10 kg/cm²×1.5 hours. Then, a cast molded plate with 12 mm (width)×12 cm (length)×1.3 mm (thickness) was obtained. The results of measurement of various properties of the oligomer 5cA and the cast molded plate are set forth in Table 1 and Table 2.

COMPARISON EXAMPLE 1

Using 4.5 g of imide type thermosetting type imide oligomer commercially available, press molding was carried out under 230° C.×10 kg/cm²×1.5 hours. Then, a cast molded plate with 12 mm (width)×12 cm (length)×1.3 mm (thickness) was obtained. The results of measurement of various properties of the imide oligomer and the cast molded plate are set forth in Table 1 and Table 2.

EXAMPLE 4

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to the reaction system, replacement with argon was sufficiently made. The reaction system was cooled to freezing temperature, and 30 ml of dried pyridine were added while paying attention to heat generation. 15 g (78 mmol) of TMA were completely dissolved in 100 ml dried DMF, and then it is added in 30 min. At that temperature, reaction was continued, and 13.1 g (39 mmol) of the aromatic diol 1aB which was dissolved in 30 ml dried DMF, were added dropwise at freezing temperature. After 30 min., an ice bath was removed, the reaction was continued for 1 hour at room temperature. Thereafter, the reaction system was again cooled to freezing temperature, and 22.8 g (78.0 mmol) of the aromatic diamine 3aB were added to 5 ml dried DMF. After 30 min., the ice bath was removed, the reaction system was heated to 60° C. using an oil bath and the reaction was continued for 30 min. 12.8 g (78.0 mmol) of the aromatic acid anhydride 4aB were added to 10 ml dried DMF and reacted for 2.6 hours. Then, 200 ml dried benzene were added and 1.4 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5aB was filtered under reduced pressure and dried for 48 hours at 80° C. in vacuum, 60.5 g (yield; 97.1%) of pale yellow powder were obtained.

Using 4.5 g of this esterimide oligomer 5aB, press molding was carried out under 230° C.×10 kg/cm²×1.5 hours. Then, a cast molded plate with 12 mm (width)×12 cm (length)×1.3 mm (thickness) was obtained. The results of measurement of various properties of the esterimide oligomer 5aB and the cast molded plate are given in Table 3 and Table 4.

EXAMPLE 5

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to the reaction system, replacement with argon were sufficiently made. The reaction system was cooled to freezing temperature, and 30 ml of dried pyridine were added while paying attention to heat generation. 15 g (78 mmol) of TMA were completely dissolved in 110 ml dried DMF, and then it was added in 30 min. At that temperature, the reaction was continued, and 9.76 g (39 mmol) of the aromatic diol 1bB, which was dissolved in 30 ml dried DMF, were added dropwise at freezing temperature. After 30 min., an ice bath was removed, the reaction was continued for 1 hour at room temperature. Thereafter, the reaction system was again cooled to freezing temperature, and 26.1 g (78.0 mmol) of the aromatic diamine 3bB were added to 50 ml dried DMF. After 30 min., the ice bath was removed, the reaction system was heated to 60° C. using an oil bath and the reaction was continued for 30 min. 13.4 g (78.0 mmol) of the aromatic acid anhydride 4bB were added to 10 ml dried DMF and reacted for 2.6 hours. Then, 200 ml dried benzene were added and 1.1 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5bB was filtered under reduced pressure and dried for 48 hours at 80° C. in vacuum, 57.6 g (yield; 92.5%) of pale yellow powder were obtained.

Using 4.5 g of this esterimide oligomer 5bB, press molding was carried out under 230° C.×10 kg/cm²×1.5 hours. Then, a cast molded plate with 12 mm (width)×12 cm (length)×1.2 mm (thickness) was obtained. The results of measurement of various properties of the esterimide oligomer 5bB and the cast molded plate are given in Table 3 and Table 4.

EXAMPLE 6

A three way cock, a Dean-Stark distillation device, a Dimroth reflux condenser and a Septum cap were attached to a 1-liter four neck flask. The reactor was dried under reduced pressure. After 14.9 g (78 mmol) of TsCl were added to reaction system, replacement with argon was sufficiently made.

The reaction system was cooled to freezing temperature, and 30 ml of dried pyridine were added while paying attention to heat generation. 15 g (78 mmol) of TMA were completely dissolved in 110 ml dried DMF, and then it was added in 30 min. At that temperature, the reaction was continued, and 20.3 g (39 mmol) of the aromatic diol 1cB, which was dissolved in 30 ml dried DMF, were added dropwise at freezing temperature. After 30 min., an ice bath was removed, the reaction was continued for 1 hour at room temperature. Thereafter, the reaction system was again cooled to freezing temperature, and 19.3 g (78.0 mmol) of the aromatic diamine 3cB were added to 50 ml dried DMF. After 30 min., the ice bath was removed, the reaction system was heated to 60° C. using an oil bath and the reaction was continued for 30 min. 12.8 g (78.0 mmol) of the aromatic acid anhydride 4aB were added to 10 ml dried DMF and reacted for 2.6 hours. Then, 200 ml dried benzene were added and 1.2 ml (theoretical quantity; 1.4 ml) of water were removed at 145° C. (bath temperature) under azeotropic conditions. After the reaction, the resultant reaction solution was poured into 1000 ml methanol and an esterimide oligomer was precipitated. When the precipitated esterimide oligomer 5cB was filtered under reduced pressure and dried for 48 hours at 80° C. in vacuum, 58.3 g (yield; 88.3%) of pale yellow powder were obtained.

Using 4.5 g of this esterimide oligomer 5cB, press molding was carried out under 230° C.×10 kg/cm₂×1.5 hours. Then, a cast molded plate with 12 mm (width)×12 cm (length)×1.5 mm (thickness) was obtained. The results of measurement of various properties of the esterimide oligomer 5cB and the cast molded plate are given in Table 3 and Table 4.

A reactive esterimide oligomer of the present invention has excellent workability resulting from high resin fluidity and provides hard substances having extremely high heat resistance. In addition, the reactive esterimide oligomer of the present invention has excellent mechanical strength, dimensional stability and electric properties. Especially, it has excellent insolubility to solvents, adhesion property with other substances and flexibility, and provides a polyesterimide which is difficult to generate voids and cracks in molded products.

As mentioned above, a reactive esterimide oligomer of the present invention has many characteristics mentioned above, so that it can provide materials extremely high in engineering value for wide usage such as for lamination plates, heat resistant paints, polymer materials for electronic devices and molding materials, and its usefulness is extremely great.

TABLE 1

|  | NMP | DMAc | DMF | THF | dioxane | MEK | CHCl₃ | HMPA | m-cresol | CH₃OH |
|---|---|---|---|---|---|---|---|---|---|---|
| Example 1 | ⊚ | ⊚ | ⊚ | ⊚ | ⊚ | Δ | ⊚ | ⊚ | ⊚ | Δ |
| 2 | ⊚ | ⊚ | ⊚ | ⊚ | ⊚ | Δ | ⊚ | ⊚ | ⊚ | Δ |
| 3 | ⊚ | ⊚ | ⊚ | ⊚ | ⊚ | ⊚ | ⊚ | ⊚ | ⊚ | Δ |
| Comp. Example 1 | ⊚ | ⊚ | ⊚ | Δ | Δ | X | X | X | Δ | X |

⊚: easily soluble, Δ: partly soluble, X: insoluble
NMP; N-methyl-2-pyrrolidone
DMAc; N,N-dimethylacetamide
DMF; N,N-dimethylformamide
THF; tetrahydrofuran
MEK; methyl ethyl ketone
HMPA; hexamethylene phosphoric triamide

TABLE 2

| | Properties of polymer | | Properties of cast molded plate | | | | |
|---|---|---|---|---|---|---|---|
| | Tg (°C.) | Td (°C.) | Density | Flexural strength | Flexural elastic modulus | Impact strength | Tg (°C.) |
| Example 1 | 232 | 512 | 1.9 | 4.3 | 333 | 3. 3.1 | 289 |
| 2 | 244 | 500 | 1.6 | 3.7 | 325 | 3. 3.4 | 287 |
| 3 | 217 | 487 | 1.7 | 4.2 | 313 | 3. 3.5 | 305 |
| Comp. Example 1 | 156 | 483 | 1.7 | 3.5 | 289 | 2. 2.6 | 265 |

Tg (°C.); Glass transition temperature (measured by Shimazu DT-40 manufactured by Shimazu Co. Ltd.)
Td (°C.); 5 weight % decreasing temperature (measured by Shimazu DT-40 manufactured by Shimazu Co. Ltd.)
Density; g/cm$^3$
Flexural strength; kg/mm$^2$
Flexural elastic modulus; kg/mm$^2$
Impact strength; kg · cm/cm$^2$ (measured by "DYNESTAT" Impact Tester manufactured by Toyo Seiki Co., Ltd.)
Tg (°C.) of the cast molded plate; Glass transition temperature (measured by "RHEOLGRAPH solid" manufactured by Toyo Seiki Co., Ltd.)

TABLE 3

| | NMP | DMAc | DMF | THF | dioxane | MEK | CHCl$_3$ | HMPA | m-cresol | CH$_3$OH |
|---|---|---|---|---|---|---|---|---|---|---|
| Example 4 | ⊚ | ⊚ | ⊚ | ⊚ | ⊚ | Δ | ⊚ | ⊚ | ⊚ | Δ |
| 5 | ⊚ | ⊚ | ⊚ | ⊚ | ⊚ | ⊚ | ⊚ | ⊚ | ⊚ | ⊚ |
| 6 | ⊚ | ⊚ | ⊚ | ⊚ | ⊚ | ⊚ | ⊚ | ⊚ | ⊚ | ⊚ |
| Comp. Example 1 | ⊚ | ⊚ | ⊚ | Δ | Δ | X | X | X | Δ | X |

⊚; easily soluble, Δ; partly soluble, X; insoluble
NMP; N-methyl-2-pyrrolidone
DMAc; N,N-dimethylacetamide
DMF; N,N-dimethylformamide
THF; tetrahydrofuran
MEK; methyl ethyl ketone
HMPA; hexamethylene phosphoric triamide

TABLE 4

| | Properties of polymer | | Properties of cast molded plate | | | | |
|---|---|---|---|---|---|---|---|
| | Tg (°C.) | Td (°C.) | Density | Flexural strength | Flexural elastic modulus | Impact strength | Tg (°C.) |
| Example 4 | 213 | 502 | 1.9 | 3.6 | 333 | 3.1 | 265 |
| 5 | 189 | 483 | 1.6 | 3.7 | 313 | 3.4 | 286 |
| 6 | 165 | 398 | 1.7 | 3.2 | 313 | 3.5 | 253 |
| Comp. Example 1 | 156 | 483 | 1.7 | 3.5 | 289 | 2.6 | 265 |

Tg (°C.); Glass transition temperature (measured by Shimazu DT-40 manufactured by Shimazu Co. Ltd.)
Td (°C.); 5 weight % decreasing temperature (measured by Shimazu DT-40 manufactured by Shimazu Co. Ltd.)
Density; g/cm$^3$
Flexural strength; kg/mm$^2$
Flexural elastic modulus; kg/mm$^2$
Impact strength; kg · cm/cm$^2$ (measured by "DYNESTAT" Impact Tester manufactured by Toyo Seiki Co., Ltd.)
Tg (°C.) of the cast molded plate; Glass transition temperature (measured by "RHEOLGRAPH solid" manufactured by Toyo Seiki Co., Ltd.)

What is claimed is:

1. A thermosetting compound, comprising a compound of the formula (IA):

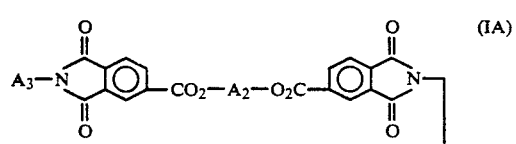

(IA)

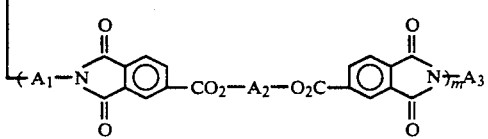

wherein A$_1$ and A$_2$ are divalent organic groups, A$_3$ is a monovalent group and A$_1$ and A$_2$ are the same or different, and m is an integer of 1-30, wherein A$_3$ is at least one member selected from the group consisting of

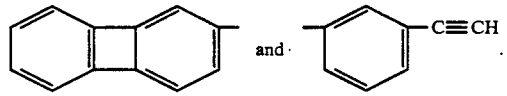

and

2. A thermosetting compound comprising a compound of the formula (IB):

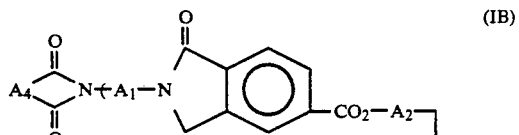

(IB)

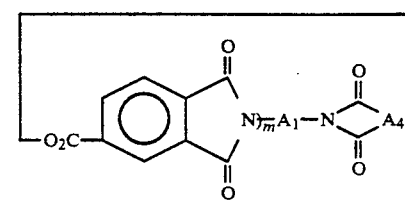

wherein $A_1$, $A_2$ and $A$ are divalent organic groups, and $A_1$, $A_2$ and $A_4$ are the same or different, and m is an integer of 1-30, wherein $A_4$ is at least one member selected from the group consisting of:

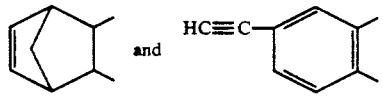

3. A thermosetting compound comprising a compound of the formula (IB):

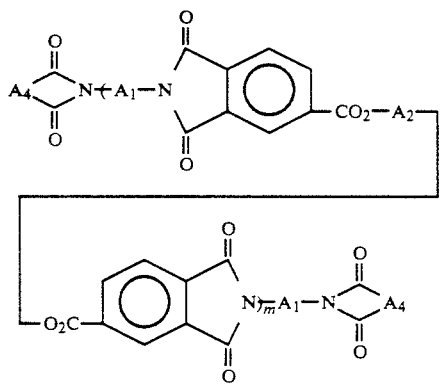

wherein $A_1$ and $A_2$ are divalent organic groups, $A_4$ is a divalent organic group selected from the group consisting of:

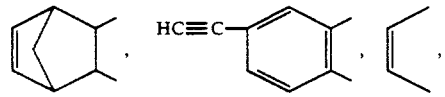

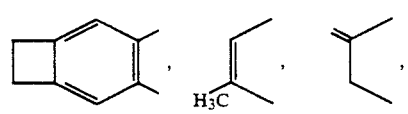

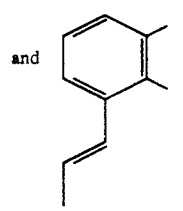

and $A_1$, $A_2$ and $A_4$ are the same or different and m is an integer of 1-30.

4. A thermosetting compound comprising a compound of the formula (IA):

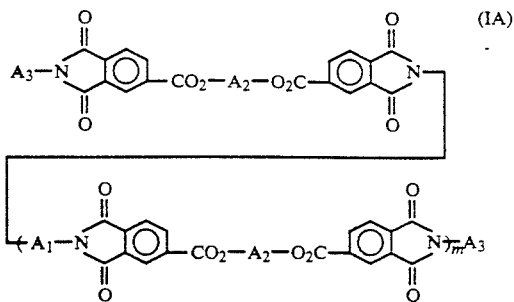

wherein $A_1$ and $A_2$ are divalent organic groups, $A_3$ is a monovalent organic group selected from the group consisting of:

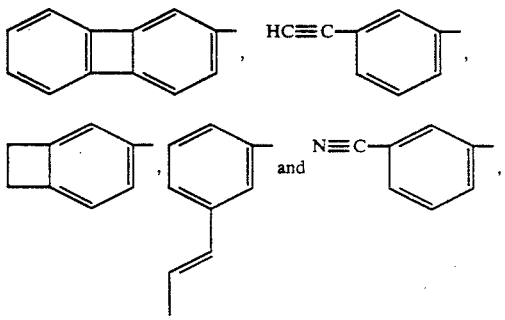

and $A_1$ and $A_2$ are the same or different and m is an integer of 1-30.

5. A thermosetting compound as claimed in claim 4 or 3, wherein $A_1$ is at least one selected from the group consisting of:

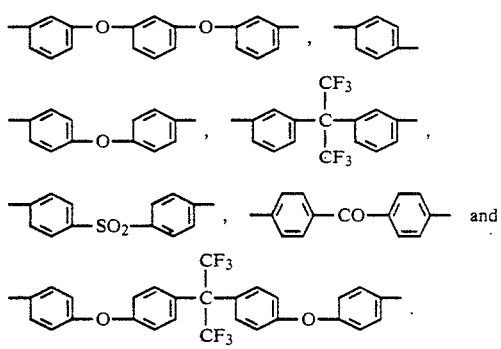

6. A thermosetting compound as claimed in claim 4 or 3, wherein $A_2$ is at least one member selected from the group consisting of:

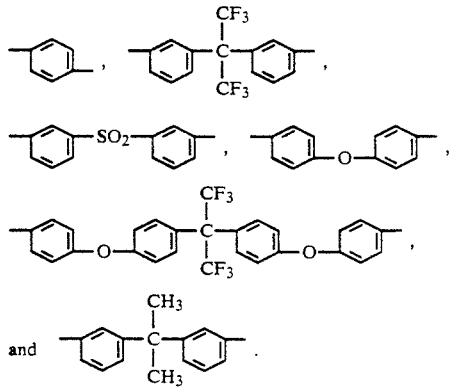

* * * * *